(12) United States Patent
Wei et al.

(10) Patent No.: US 6,899,947 B2
(45) Date of Patent: May 31, 2005

(54) NANOPARTICLE ARRAYS AND SENSORS USING SAME

(75) Inventors: Alexander Wei, West Lafayette, IN (US); Beomseok Kim, West Lafayette, IN (US)

(73) Assignee: Purdue Research Foundation, West Lafayette, IN (US)

(*) Notice: Subject to any disclaimer, the term of this patent is extended or adjusted under 35 U.S.C. 154(b) by 22 days.

(21) Appl. No.: 10/218,185

(22) Filed: Aug. 12, 2002

(65) Prior Publication Data

US 2003/0068496 A1 Apr. 10, 2003

Related U.S. Application Data

(60) Provisional application No. 60/312,097, filed on Aug. 14, 2001.

(51) Int. Cl.[7] .............................. B05D 7/00; B32B 5/16
(52) U.S. Cl. ...................... 428/323; 428/328; 428/402; 428/402.24; 428/403; 427/212
(58) Field of Search ................. 428/323, 328, 428/402.24, 403, 402, 212

(56) References Cited

U.S. PATENT DOCUMENTS 5,688,998 A * 11/1997 Ichimura et al. ............ 562/466

FOREIGN PATENT DOCUMENTS

EP           1293248 A1 * 3/2003 ............ B01J/13/00

OTHER PUBLICATIONS

Michael D. Musick, Christine D. Keating, Melinda, H. Keefe, and Michael J. Natan; *Stepwise Construction of Conductive Au Colliod Multilayers from Solution*; Chem. Mater., vol. 9, No. 7 (1997); pp. 1499–1501.

J. Schmitt, P. Machtle, D. Eck, H. Mohwald, and C.A. Helm; *Preparation and Optical Properties of Colloidal Gold Monolayers*; Langmuir, vol. 15, No. 9 (1999); pp. 3256–3266.

Kenneth R. Brown, Daniel G. Walter, and Michael J. Natan; *Seeding of Colloidal Au Nanoparticle Solutions. 2. Improved Control of Particle Size and Shape*; Chem. Mater., vol. 12, No. 2 (2000); pp. 306–313.

Peter M. Tessier, Orlin D. Velev, Anand T. Kalambur, John F. Rabolt, Abraham M. Lenhoff, and Eric W. Kaler; *Assembly of Gold Nanostructured Films Templated by Colloidal Crystals and Use in Surface–Enhanced Raman Spectroscopy*; J. Am. Chem. Soc., vol. 122, No. 39 (2000); pp. 9554–9555.

Alexander Wei, Beomseok Kim, Bryce Sadtler, and Steven L. Tripp; *Tunable Surface–Enhanced Raman Scattering from Large Gold Nanoparticle Arrays*; Chem. Phys. Chem., No. 12 (2001), 743–745.

R. Balasubramanian, Beomseok Kim, Steven L. Tripp, Xuejun Wang, Marya Lieberman, and Alexander Wei; *Dispersion and Stability Studies of Resorcinarene–Encapsulated Gold Nanoparticles*; Langmuir, vol. 18, No. 9 (2002); pp. 3676–3681 and includes supporting information pp. S1–S5.

* cited by examiner

Primary Examiner—Monique R. Jackson

(57) ABSTRACT

A method for enhancing the dispersibility of calixarene-stabilized nanoparticles, which can be assembled into ordered, planar arrays of monoparticulate thickness, ring-like assemblies of discrete particle count, and other configurations.

16 Claims, 8 Drawing Sheets

1: X=CH$_2$SH, R=-CH$_2^-$
2: X=SH, R=-CH$_2^-$
3: X=Br, R=-CH$_2^-$
4: X=H, R=H

NANOPARTICLE ARRAYS AND SENSORS USING SAME

This application claims the benefits of U.S. provisional application Ser. No. 60/312,097 filed Aug. 14, 2001.

FIELD OF THE INVENTION

The present invention relates to a method for enhancing the dispersibility of nanoparticles, which can be applied toward the formation of 2D nanoparticle assemblies and arrays with an ordered structure as well as sensors using same.

BACKGROUND OF THE INVENTION

The dispersion and self-assembly of nanoparticles are considered by many to be key methodologies in materials synthesis. For example, the next generation of materials for nanoscale electronic and other devices may require production and use of nanoscale particles, such as nanoscale metallic particles, which should be resistant to environmental degradation and amenable to synthesis in the form of nanostructured materials. For example, the spontaneous assembly of monolayer-protected nanoparticles into periodic two-dimensional (2D) arrays is of interest since many such arrays may demonstrate novel optical and/or electronic properties as a function of particle size, composition and interparticle spacing in the array that may of use in optical/infrared scattering, radiation shielding, or sensing.

Hydrophobic surfactants such as alkanethiols have been used to drive the nanoparticles toward self-assembly at an aqueous interface; however, 2D array formation by this technique has so far been limited to small (less than 10 nm) nanoparticles. Stabilized metal particles beyond this threshold become increasingly prone to multi-layer or three-dimensional aggregate formation, which can be attributed to the rapid increase in van der Waals attraction between particles as a function of size and interatomic pair potentials.

SUMMARY OF THE INVENTION

The present invention provides a method for enhancing the dispersibility of calixarene-stabilized nanoparticles, which can be assembled into ordered, planar arrays of monoparticulate thickness, ring-like assemblies of discrete particle count, and other technologically useful configurations.

In practicing an illustrative embodiment of the invention, a nanoparticle is treated with calixarenes, such as resorcinarenes, more preferably tetrathiol resorcinarenes, having a macrocyclic, concave, multi-valent headgroup with multiple hydrocarbon tails per molecule with the hydrocarbon tails spaced several angstroms apart. Nanoparticles can be dispersed in liquid organic solvents or at the interface between organic and aqueous liquid solvents. Nanoparticles selected from metals, alloys, magnetic materials and semiconducting materials may used pursuant to the invention. Metal nanoparticles can be extracted from aqueous suspension and dispersed into a nonpolar organic liquid solvent medium.

In practicing an illustrative embodiment of the invention, a planar array is formed by introducing calixarene-treated nanoparticles in the size range of 15 to 200 nm (nanometers) onto an gas/liquid (e.g. air/water) interface in a container to form a self-assembled, two-dimensional (2D) film array with monoparticulate thickness and long range order, which can then be deposited as such onto a suitable substrate by relative movement of the substrate and the interface. The self-assembled, nanostructured 2D array is deposited having organized long-range order of the nanoparticles on the substrate. Optical or other properties of 2D arrays formed pursuant to the invention can be tuned as a function of particle size, particle composition, and interparticle spacing, the latter being especially influential in controlling optical and electronic properties of the arrays.

The above-described nanoparticle arrays provided pursuant to another embodiment of the invention may find use in devices and methods involving optical/infrared scattering, electromagnetic shielding, chemical sensing, chemical synthesis, and biomedical applications including drug delivery and therapeutic agents. Chemical, biomolecular and other sensors are envisioned using the above-described nanoparticle arrays pursuant to the invention.

The above objects and advantages of the invention will become apparent from the following description of the invention.

DESCRIPTION OF THE DRAWINGS

In FIGS. 1B, 1C, and 1D, the nanoparticles had an average particle diameter of 16, 34, and 87 nm, respectively. In FIGS. 1B and 1C, the arrays were transferred onto a Formvar-coated Cu grids (300 mesh) by manual Langmuir-Schaefer horizontal deposition. In FIG. 1D, the array was transferred by mechanically controlled vertical deposition onto a Formvar-coated Cu grid mounted on a glass slide which had been ionized just prior to use.

In FIG. 3A, spectra were obtained using a dispersive spectrometer at a Raman excitation wavelength of 647.1 nm by a krypton ion laser. In FIG. 3B, spectra were obtained using an FT spectrometer at a Raman excitation wavelength of 1064 nm by a Nd:VO$_4$ laser.

In FIGS. 4A and 4B, particle size is 42 and 70 nm, respectively. In FIGS. 4C and 4D, particle size is 111 and 170 nm, respectively. In FIGS. 4A and 4B, the arrays were transferred onto a Formvar-coated Cu grids (300 mesh) by manual Langmuir-Schaefer horizontal deposition. In FIGS. 4C and 4D, the arrays were transferred by mechanically controlled vertical deposition onto a Formvar-coated Cu grid mounted on a glass slide which had been ionized just prior to use.

DESCRIPTION OF THE INVENTION

The robustness and dispersion control of nanoparticles in various solvents (liquid media) are enhanced by employing calixarenes as stabilizing surfactants. The invention provides in one embodiment an inexpensive and reliable procedure for fabricating highly ordered, monoparticulate nanoparticle arrays and assemblies with valuable optical properties, and nanoparticle rings with unusual magnetic characteristics. These physical properties can be tuned as a function of particle size, composition, and interparticle spacing. The invention provides in another embodiment a method for encapsulating nanoparticles in robust (strongly attached), nondesorptive shells, which can be used in a variety of applications including organic synthesis, drug delivery, and chemical and biological separations.

Calixarenes are characterized by macrocyclic polyaromatic headgroups connected to several hydrocarbon tails (tailgroups) as described by V. Bohmer in "Calixarenes Macrocycles with (Almost) Unlimited Possibilities", Angew. Chem. Int. Ed. Engl. 34, 713–745, 1995, the teachings of which are incorporated herein by reference. Calixarene is a macrocycle formed by the condensation of phenolic and heterocyclic units and aldehydes or derivatives thereof, characterized by a concavity (headgroup) often rimmed with heteroatoms (N, O, P, S, Cl, Se, Br, and I) or functional groups containing such atoms, and multiple substituents (tailgroups) of hydrocarbon chains, aromatic rings, polyether chains, or combinations thereof. These can also be functionalized with heteroatoms or functional groups containing such atoms. Examples include resorcinol (1,3 hydroxybenzene)-derived calixarenes (resorcinarenes and cavitands), pyridine-derived calixarenes (pyridene-arenes), and pyrrole-derived calixarenes (calix-pyrroles). Exemplary calixarenes comprise resorcinol-derived calixarenes (resorcinarenes) with various functional groups attached either to the macrocylic headgroup (e.g. R, X=H, $CH_3$, $CH_2SH$, $PPh_2$, $CS_2$, $CH_2N$-dialkyl, $CH_2N$-alkyl-$CS_2$) or the tailgroups (e.g. terminal olefins, amines, thiols, alcohols, carboxylates, and other functional groups or derivatives thereof).

Pursuant to the invention, adsorption of calixarene molecules to the nanoparticle surfaces renders them hydrophobic and highly repulsive at close range. This repulsion is partly due to entropic factors; the spacing of the tails precludes dense packing and increases the overall conformational entropy of the surfactant layer, thereby raising the barrier against steric compression. Excellent dispersing properties have been demonstrated using resorcinarenes, a class of calixarenes derived from resorcinol, which were able to stabilize dispersions of large gold nanoparticles in hydrocarbon liquid solutions.

Figure 1A:
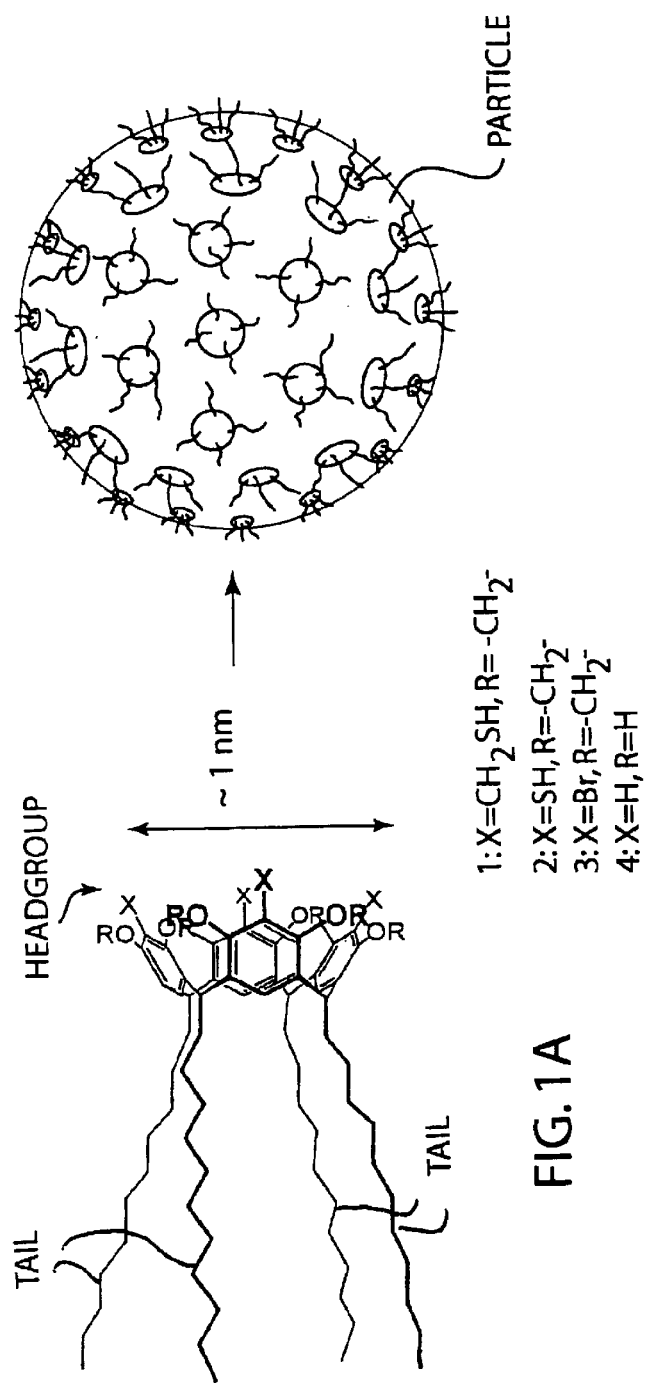
FIG. 1A is a diagram of a gold nanoparticle being treated with resorcinarene designated 1, 2, 3, or 4.

For purposes of illustration and not limitation, a method for fabricating monoparticulate films via the self-organization uses calixarene surfactants designed to promote the self-organization of metal (e.g. gold) nanoparticles up to 170 nm (nanometer) in diameter into hexagonally close-packed (hcp) arrays at the air-water interface. The formation of well-ordered arrays or assemblies from large gold nanoparticles is used herein for demonstrating this methodology, since nearly all materials possess Hamaker constants smaller than that of gold and therefore are not as strongly affected by attractive interparticle forces. For purposes of illustration and not limitation, resorcinarene-derived surfactants with sulfur-functionalized headgroups; i.e. tetrabenzylthiol C11 resorcinarene 1 and tetraarylthiol C11 resorcinarene 2 were used extract and disperse colloidal gold nanoparticles up to nearly 100 nm from aqueous suspensions into nonpolar liquid solvent media. These resorcinarene molecules have a large, macrocyclic, concave, multi-valent headgroup with multiple hydrocarbon tails per molecule with the hydrocarbon tails spaced several angstroms apart (e.g. see FIG. 1A). The synthesis of tetrathiol resorcinarene 1 as well as tetraarylthiol resorcinarene 2 is described below under Synthesis Procedures and in the literature for closely related molecules, such as in Moran et al. "Cavitands Synthetic Molecule Vessels", J. Am. Chem. Soc. 104, 5826–5828, 1982, and Gibb et al. "Efficient coupling of amino acid derivatives to rigid organic scaffolds: model syntheses for de novo proteins", Tetrahedron 51, 8719–8732, 1995. For example, tetrabenzylthiol C11 resorcinarene 1 was synthesized by O,O-methylenation of tetra (2-methyl) resorcinarene at elevated temperature and pressure, followed by bromination of the metyl groups and treatment with thiourea. Tetraarylthiol resorcinarene 2 was prepared by lithium-halogen exchange of the corresponding tetrabromide followed by treatment with elemental sulfur.

Preparation of Monoparticulate Films of Large Gold Nanoparticles

Subpicomolar aqueous ($10^9$–$10^{11}$ particles/mL) of citrate-stabilized gold nanoparticles of narrow size dispersity with relative standard deviations (RSDs) of $\leq$20% purchased from British Biocell International were treated briefly with a mixed-bed ion-exchange resin (Amberlite MB-3 available from Mallinckrodt Co.), then transferred to a silanized test tube and mixed vigorously with a 1 mM solution resorcinarene 2 in THF in equal proportions (16–42 nm particles) or in a 3:4 ratio (70–170 nm particles). The number of particles used was roughly 150% the estimated amount necessary to form an hcp monoparticulate film across the air-water interface. The mixture was extracted several times against toluene to remove THF and excess surfactant. The resorcinarene-coated nanoparticles were flocculated at the solvent interface and were densified by drawing the aqueous suspension into a silanized glass pipet, then carefully draining the supernatant until a minimal volume was achieved. The remaining suspension was spread across the air-water interface of a test tube and allowed to sit undisturbed for at least 30 minutes to allow for the complete evaporation of toluene. The resulting monoparticulate film was highly reflective and contained domains which appeared uniform to the naked eye.

Transfer of Gold Nanoparticle Arrays

The monoparticulate films were transferred at the air-water interface onto Formvar-coated TEM grids either by the manual horizontal deposition commonly known as the Langmuir-Schaefer technique, or by slow (1 mm/mm) vertical retraction (lifting) of a partially immersed substrate through the air-water interface using a mechanically controlled deposition arm available from Kibron, Inc. connected to the upper end of the substrate. The substrates were either heat-annealed quartz slides soaked in piranha solution just prior to deposition, or Formvar-coated TEM grids mounted on glass substrates and ionized just before use. AFM linescan analysis of the quartz substrates indicated a peak-to-valley roughness of approximately 1 nm. Films on quartz substrates were inspected for regions of optical uniformity at 40× magnification prior to SERS analysis (see below).

TEM Analysis

Figure 1D:
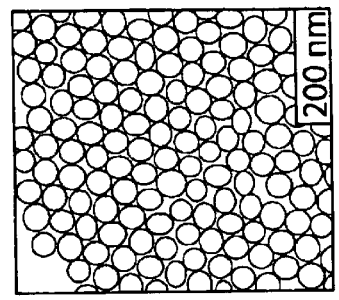
FIGS. 1B, 1C, and 1D each is a representation of a transmission electron micrograph (TEM) of a self-assembled 2D nanoparticle array of encapsulated gold particles on Formvar-coated Cu grids pursuant to the invention.
Figure 1C:
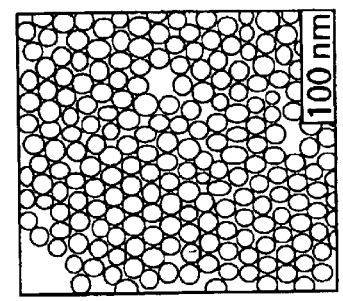
Figure 1B:
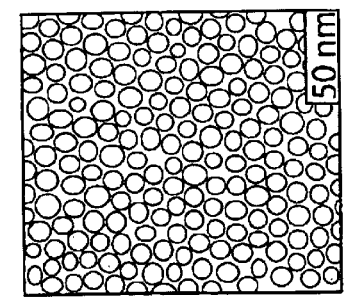
Figure 4A:
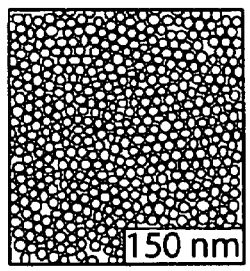
FIGS. 4A, 4B, 4C, and 4D each is a representation of a transmission electron micrograph (TEM) of a self-assembled 2D nanoparticle planar array of encapsulated gold particles pursuant to the invention.
Figure 4B:
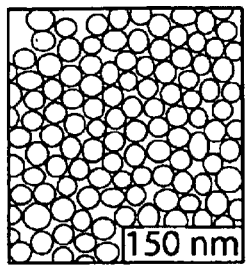
Figure 4C:
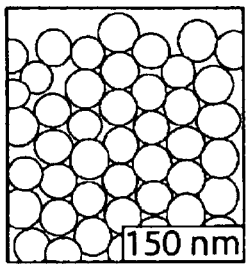
Figure 4D:
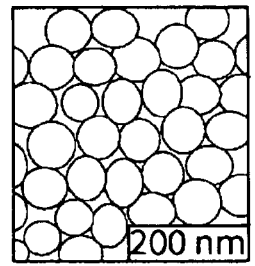

Gold nanoparticle arrays transferred onto Formvar-coated Cu grids (300 mesh) were analyzed by TEM using a Philips EM-300 at accelerating voltages of 80 or 100 kV. Particle arrays were transferred either by horizontal deposition (average particle diameters are 16, 34, 42 and 70 nm, see FIGS. 4A, 4B and FIGS. 1B, 1C) or by vertical deposition (average particle diameters are 87, 111 and 170 nm, see FIGS. 4C, 4D and FIG. 1D). TEM analyses were always performed shortly after array transfer. A number of particles appear to be fused; however, the majority of these (>95%) are single particles with slight lateral overlap as a result of size dispersity, whose edges can be distinguished in the original images. The occasional truly fused particles are most likely due to sintering by the high-energy electron beam during analysis.

Figure 5:
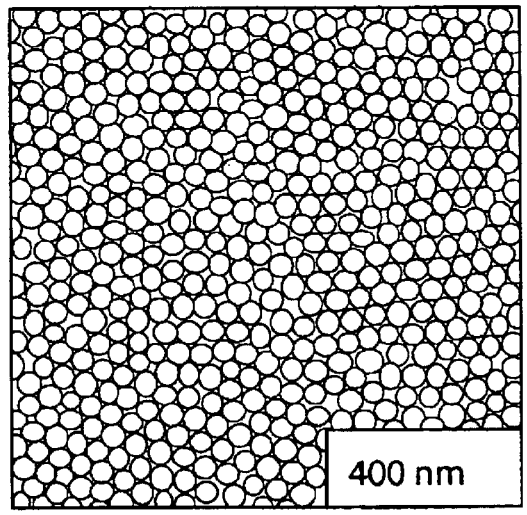
FIG. 5 is a representation of a transmission electron micrograph (TEM) of a self-assembled 2D nanoparticle array of encapsulated gold particles pursuant to the invention where particle size is 70 nm.

Average particle diameters (d) were calculated from the digitized areas of individual nanoparticles within the array ($N \geq 100$) using a size analysis program (SigmaScan 5.0, SPSS). With the exception of the 16 nm particles, the RSDs (relative standard deviations) were all less than 10%, indicating that the particles in the arrays were self-selecting. Fast Fourier transforms (FFTs) were performed using an Adobe Photoshop plug-in (Image Processing Toolkit, Reindeer Games). FFT analysis yielded average periodicities which were comparable to or less than d, primarily because of apparent particle overlap and other defects in lattice structure (see FIG. 5, Table A). Errors based on calculations from the various harmonics in a given transform (typically first through third) were between 6% and 15%; these were also too significant to allow meaningful estimates of interparticle distances, which were 1-5% that of d. Therefore, average interparticle spacing parameters ($\delta$) were determined from the digitized distances between nearest-neighbor particles (N=25) using a standard graphics software package (Adobe Photoshop 5.0 Adobe Systems). Indeterminate errors caused by differences in focal length or image editing were found to be insignificant compared to the digital resolution of the images (0.22 nm/pixel) and the standard deviations (0.14–0.31 nm). The latter measurements were restricted to spacings between non-overlapping particles completely embedded within a hcp (hexagonal close packed) lattice, and were thus able to generate distance parameters with a greater degree of precision. Although these values are not representative of the entire array, the relative trend in $\delta$ with increasing periodicity is unmistakable. The interparticle spacing values of Table A demonstrate a trend toward decreasing interparticle spacing with increasing periodicity.

Figure 6:
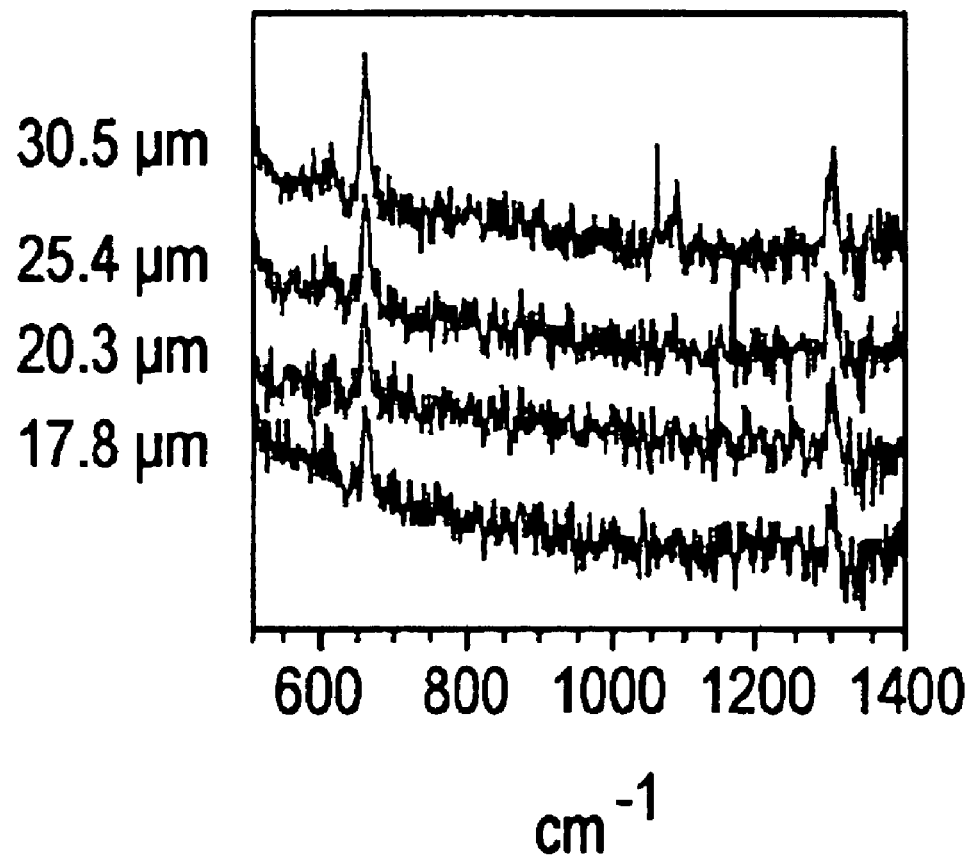
FIG. 6 shows unenhanced Raman spectra of resorcinarene tetrabromide 3 as a function of film thickness where small quantities of the compound were placed on a quartz substrate and heated slowly on a hot plate until melted, then were pressed into a thin film using a glass cover slip. Film thicknesses were measured using a micrometer with a resolution of 0.1 micron. Spectra were obtained using a dispersive Raman microscope with a 10× objective lens at an excitation wavelength and power of 785 nm and 20 mW by a diode laser (SDL).

Estimation of Surface Enhancement Factors in SERS:

Empirical signal enhancement factors were determined by comparing the peak area integrations centered at 813 cm$^{-1}$ from resorcinarene tetrathiol 2 adsorbed on the gold nanoparticle arrays with the corresponding peak integrations centered at 651 cm$^{-1}$ from unenhanced films of resorcinarene tetrabromide 3. Compounds 2 and 3 have very similar characteristic Raman group frequencies (equivalent peak in solid 1 is at 663 cm$^{-1}$), but resorcinarene tetrabromide 3 was used as a reference because of its greater chemical and thermal stability. A standard graphing software package (KaleidaGraph, Synergy) was used to perform data manipulations and peak integrations. Films of variable thicknesses (18–30.5 microns±0.5 micron, see FIG. 6) were measured to ascertain that signal intensities increased in proportion with film thickness, allowing us to estimate the unenhanced Raman signals in terms of molecular density per unit area. The density of resorcinarene tetrabromide 3 in a liquid (melt) state was determined to be 1.13±0.23 g/ml, corresponding to an areal density of 1.48×10$^{18}$ molecules/cm$^2$ in a 30.5 micron film. Obtaining areal densities of resorcinarene tetrathiol 2 adsorbed to the nanoparticle arrays required some simplifying assumptions: (i) the nanoparticle arrays all have approximately equal surface roughness (1.8 for an ideally planar hcp array); (ii) the SERS signals are spatially averaged and can be quantified as a function of areal density of the adsorbate; (iii) a high percentage of the nanostructured surfaces are passivated by resorcinarene tetrathiol 1 with an average surface density of 2 nm$^2$/molecule, corresponding to approximately 75% particle coverage and an areal density of 6×10$^{13}$ molecules/cm$^2$. The signal enhancement factor G can then be quantified as:

$$G = \frac{S^{array}}{S^{thin\,film}} \left( \frac{D^{thin\,film}}{D^{array}} \right) = 2.46 \times 10^4 \cdot \frac{S^{array}}{S^{thin\,film}}$$

where S and D are the integrated signal and molecular density per unit area of the resorcinarenes in the unenhanced (thin film) and surface-enhanced (array) samples. It is important to note that the enhanced Raman scattering cross sections may vary greatly between molecules depending on their site of adsorption (see main text); therefore, signal enhancements determined by this method are relative at best.

Multiple Raman spectra (N=9-11) of each nanoparticle array were acquired at 785 nm excitation, N.A.=0.75 at different locations on the sample to ascertain signal reproducibility. The peak integration RSDs ranged from 14 to 35% (see Tables B, C). The signal enhancements appear to be reproducible between replicate arrays, with occasional samples having anomalously strong signal. For example, three 170-nm particle arrays transferred onto glass substrates had average G values of 1.27×10$^7$, 1.28×10$^7$, and 3.18×10$^7$. Signal enhancements from other arrays (d=70 nm) were also reproducible within one standard deviation of the mean; however, many of the replicate samples contained high levels of background fluorescence with substantial baseline distortion, preventing a more comprehensive evaluation.

SERS as Function of Wavelength and Collection Angle:

Raman spectra at an excitation wavelength of 647.1 nm were recorded using a dispersive spectrometer (SpectraCode, N.A.=0.4, sampling diameter approx. 120 micron, integration time=10 sec) and a krypton ion laser (Spectra-Physics, 50 mW at the sample). Spectra at an excitation wavelength of 1064 nm were obtained using a FT spectrometer Nicolet, N.A.=0.5, sampling diameter>1000 micron, 128 scans) and a Nd:VO$_4$laser (500 mW). Spectra at an excitation wavelength of 785 nm were acquired using a home-built dispersive Raman imaging microscope and a diode laser (SDL, 315 mW). MicroRaman spectra were obtained using 10×, 20×, and 40× objective lenses (Olympus, N.A.=0.25, 0.40, and 0.75 respectively). The laser input power, which was limited by the acceptance apertures on the back side of the objectives (overfilled case), was measured to be 20 mW, 12 mW, and 10 mW at the sample, respectively.

estimate a value for S of the thin film at N.A.=0.75 relative to the signal obtained at N.A.=O.40:

$$S^{thin\,film}_{40X} = S^{thin\,film}_{20X} \left(\frac{\beta^{benzene}_{40X}}{\beta^{thin\,film}_{20X}}\right)\left(\frac{P_{40X}}{P_{20X}}\right)\left(\frac{A_{40X}}{A_{20X}}\right)\left(\frac{\Omega_{40X}}{\Omega_{20X}}\right) = 0.273 \cdot S^{thin\,film}_{20X}$$

Figure 3A:
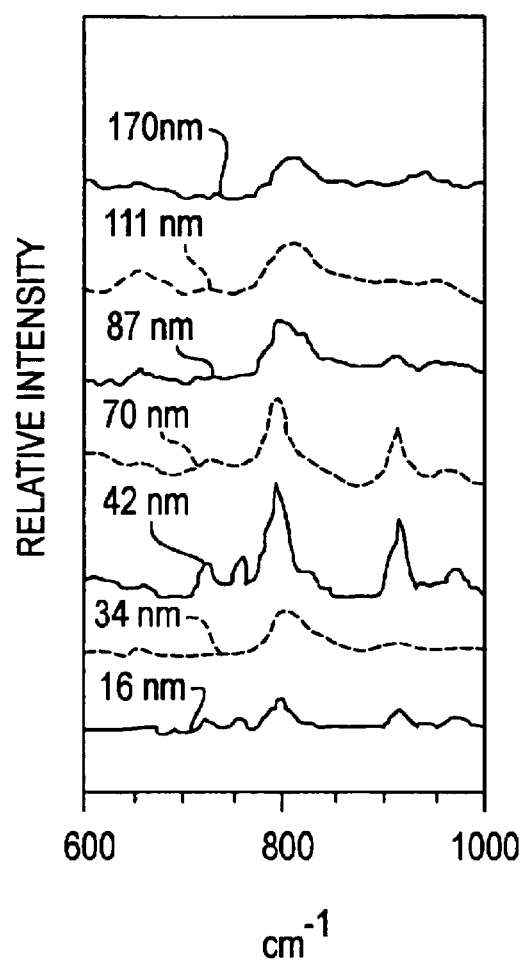
FIGS. 3A, 3B show surface-enhanced Raman scattering as a function of array structure.
Figure 3B:
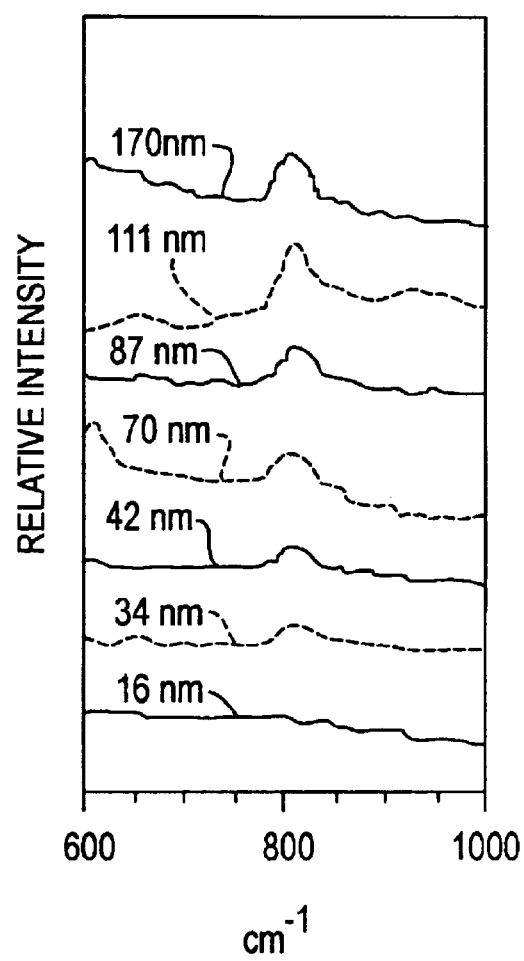
Figure 3C:
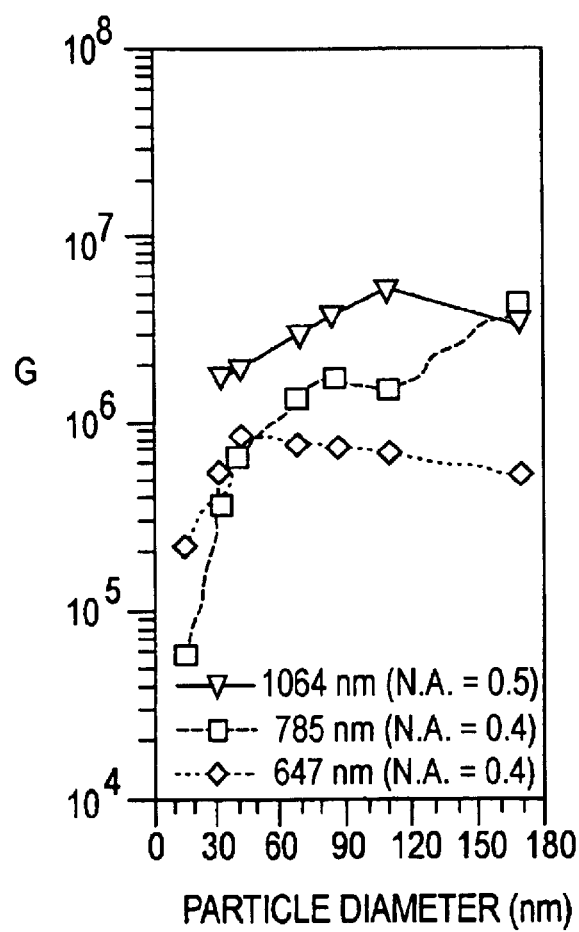
FIGS. 3C, 3D show G values (signal enhancement factors) as a function of periodic array structure and numerical aperture at a fixed excitation wavelength (785 nm). Error bars are equal to one standard deviation based on replicate measurements at different positions on the sample.
Figure 3D:
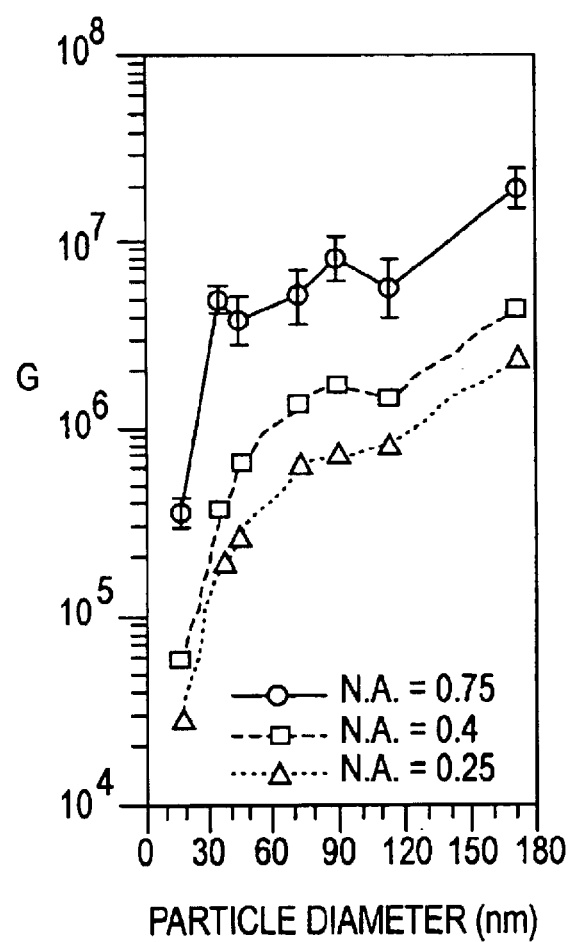

Signal enhancement factors at N.A.=0.75 were then calculated and found to be nearly an order of magnitude greater than those obtained at N.A.=0.25 (see FIG. 3D). The average relative SERS cross sections ($\beta^{SERS}$) at 20× and 40× were determined to be 3.2 and 5.0 (see Table E); the corresponding ratio of $\beta^{SERS}$ to $\beta^{thin\,film}$(the relative change in G as a function of aperture) is 2.0 and 8.7, respectively.

TABLE A

TEM analysis of hcp gold nanoparticle arrays: particle size, interparticle spacing, and FFT analysis

| average particle diameter, d (nm) | S.D. (nm) | interparticle spacing parameter (nm) | S.D. (nm) | 1st harmonic analysis (nm) | 2nd harmonic analysis (nm) | 3rd harmonic analysis (nm) | Average periodicity (nm) | S.D. (nm) |
|---|---|---|---|---|---|---|---|---|
| 15.9 | 3.0 | 1.00 | 0.31 | 16.1 | 18.5 | | 17.3 | 1.7 |
| 34.5 | 2.4 | 0.89 | 0.26 | 32.0 | 36.5 | 38.4 | 35.6 | 3.3 |
| 41.6 | 3.4 | 0.78 | 0.16 | 40.4 | 43.8 | | 41.3 | 3.0 |
| 70.0 | 5.0 | 0.64 | 0.20 | 69.7 | 73.1 | 71.9 | 71.6 | 1.7 |
| 87.4 | 6.7 | 0.57 | 0.22 | 77.7 | 84.7 | 87.4 | 82.1 | 6.2 |
| 111.5 | 7.9 | 0.40 | 0.14 | 93.2 | 116.5 | 107.6 | 105.8 | 11.8 |
| 170.2 | 12.1 | n/a | n/a | 153.4 | 170.5 | 143.9 | 155.9 | 13.5 |

Relative changes in Raman scattering cross sections as a function of aperture were determined according to the equation:

$$S=(P_D\beta DK)(A_D\Omega_D TQ)t_s$$

where $P_D$ is the laser power at the sample, $\beta$ is the Raman scattering cross section of the analyte, D is the molecular density, and K is a geometric factor defining depth of field; $A_D$ is the sampling area, $\Omega_D=\pi(N.A.)^2$ is the solid angle of collection in steradians, T is the transmission efficiency factor, Q is the quantum efficiency, and $t_s$ is the time of measurement. $A_D$, $\Omega_D$ and K (for a thick transparent sample such as neat benzene, change with the N.A. of the objective lens (see Table D). Assuming all other parameters to be constant, the changes in S/$\beta$ for the 20× and 40× objectives relative to the 10× objective are approximately 0.24 and 0.067, respectively. The relative signal intensities from neat benzene at 992 cm$^1$ for the 20× and 40× objectives were measured to be 0.362 and 0.038, yielding relative $\beta$ values of 1.5 and 0.57, respectively. It should be mentioned that these values are affected by the transmission efficiency of the objective lens itself; however, changes in signal which are not related to N.A. can be described as a single variable for the purposes of this study.

Similar comparisons were made using a thin film of resorcinarene tetrabromide 3 and the nanoparticle arrays in which K is constant with respect to N.A., so that changes in $\beta$ are only due to $P_D$, $A_D$, and $\Omega_D$. The relative change in $\beta$ for the resorcinarene thin film with tile 20× lens was determined to be almost identical to that of benzene, but it was not possible to obtain a thin film Raman signal at 40× of sufficient quality for comparison. Therefore, the relative $\beta$ from the benzene measurement at 40× was used to

TABLE B

Summary of replicate measurements of Raman peak integration at 831 cm−1 (785 nm excitation, N.A. = 0.75)

| Particle diameter | Minimum integrated area | Maximum integrated area | samples (N) | Mean | Std Deviation |
|---|---|---|---|---|---|
| 16 nm | 4326.6 | 6462.8 | 9 | 5329.9 | 872.8 |
| 34 nm | 58036 | 90838 | 9 | 73891 | 9971 |
| 42 nm | 35282 | 87440 | 9 | 56708 | 17180 |
| 70 nm | 39640 | 102230 | 9 | 77462 | 23867 |
| 87 nm | 91328 | 193410 | 11 | 127950 | 35634 |
| 111 nm | 50621 | 146510 | 9 | 84665 | 29377 |
| 170 nm | 176910 | 419880 | 10 | 283320 | 74676 |

TABLE C

Replicate measurements of Raman peak integration at 831 cm−1 (785 nm excitation, N.A. = 0.75)

| Sample no. | 16 nm | 34 nm | 42 nm | 70 nm | 87 nm | 111 nm | 170 nm |
|---|---|---|---|---|---|---|---|
| 1 | 4481 | 68903 | 68052 | 39640 | 107110 | 53718 | 309565 |
| 2 | 4700 | 67951 | 87440 | 100489 | 101649 | 50621 | 338441 |
| 3 | 5529 | 71845 | 35282 | 98144 | 123430 | 77458 | 287732 |
| 4 | 5496 | 72133 | 41365 | 73602 | 91328 | 73037 | 337689 |
| 5 | 6461 | 86001 | 44676 | 70952 | 108210 | 79689 | 236445 |
| 6 | 4327 | 79207 | 48807 | 44696 | 94453 | 109414 | 211427 |
| 7 | 4439 | 90838 | 54862 | 98804 | 155408 | 93994 | 306658 |
| 8 | 6069 | 58036 | 76063 | 70594 | 101059 | 77539 | 208453 |

TABLE C-continued

Replicate measurements of Raman peak integration at
831 cm–1 (785 nm excitation, N.A. = 0.75)

| Sample no. | 16 nm | 34 nm | 42 nm | 70 nm | 87 nm | 111 nm | 170 nm |
|---|---|---|---|---|---|---|---|
| 9 | 6463 | 70100 | 53821 | 102230 | 193410 | 146510 | 419880 |
| 10 | | | | | 172388 | | 176910 |
| 11 | | | | | 158959 | | |

TABLE D

Parameters affecting signal strength as a function of aperture

| Objective | N.A. | input power (mW) | sample area (cm^2) | collection angle (sr) | rel. depth K (f/#) | rel. benzene signal (992 cm–1) | rel. β (benzene) |
|---|---|---|---|---|---|---|---|
| 10x | 0.25 | 20 | 1.13 e–04 | 0.188 | 1.93 | 1 | 1 |
| 20x | 0.40 | 12 | 2.83 e–05 | 0.503 | 1.14 | 0.362 | 1.50 |
| 40x | 0.75 | 10 | 7.07 e–06 | 1.759 | 0.44 | 0.038 | 0.57 |

TABLE E

Relative changes in cross section (β) from resorcinarene thin film and nanoparticle arrays

| Objective | resorcinarene thin film (651 cm–1) | 16 nm array (813 cm–1) | 34 nm array (813 cm–1) | 42 nm array (813 cm–1) | 70 nm array (813 cm–1) | 87 nm array (813 cm–1) | 111 nm array (813 cm–1) | 170 nm array (813 cm–1) |
|---|---|---|---|---|---|---|---|---|
| 10x | 1 | 1 | 1 | 1 | 1 | 1 | 1 | 1 |
| 20x | 1.52 | 3.04 | 2.65 | 3.87 | 3.29 | 3.52 | 2.75 | 2.91 |
| 40x | <0.57> | 4.90 | 7.43 | 4.48 | 3.91 | 5.44 | 4.01 | 4.64 |

Surface-Enhanced Raman Scatttering (SERS) Information

Surface-enhanced Raman scattering (SERS) integrates high levels of sensitivity with spectroscopic precision and thus has tremendous potential for chemical and biomolecular sensing. Efforts to understand and develop SERS as an analytical tool are dependent on methods for fabricating materials with stable and reproducibly high activities. Typical SERS substrates such as roughened gold and silver electrodes or colloidal aggregates are disordered and often produce unpredictable signal enhancements; moreover, their structures are unstable and quickly lose their SERS activity. Controlled methods for preparing nanostructured metal substrates may provide more useful correlations between surface structure and signal enhancement. The particle size and interparticle spacing are primary considerations for strong SERS activity.

Figure 2:
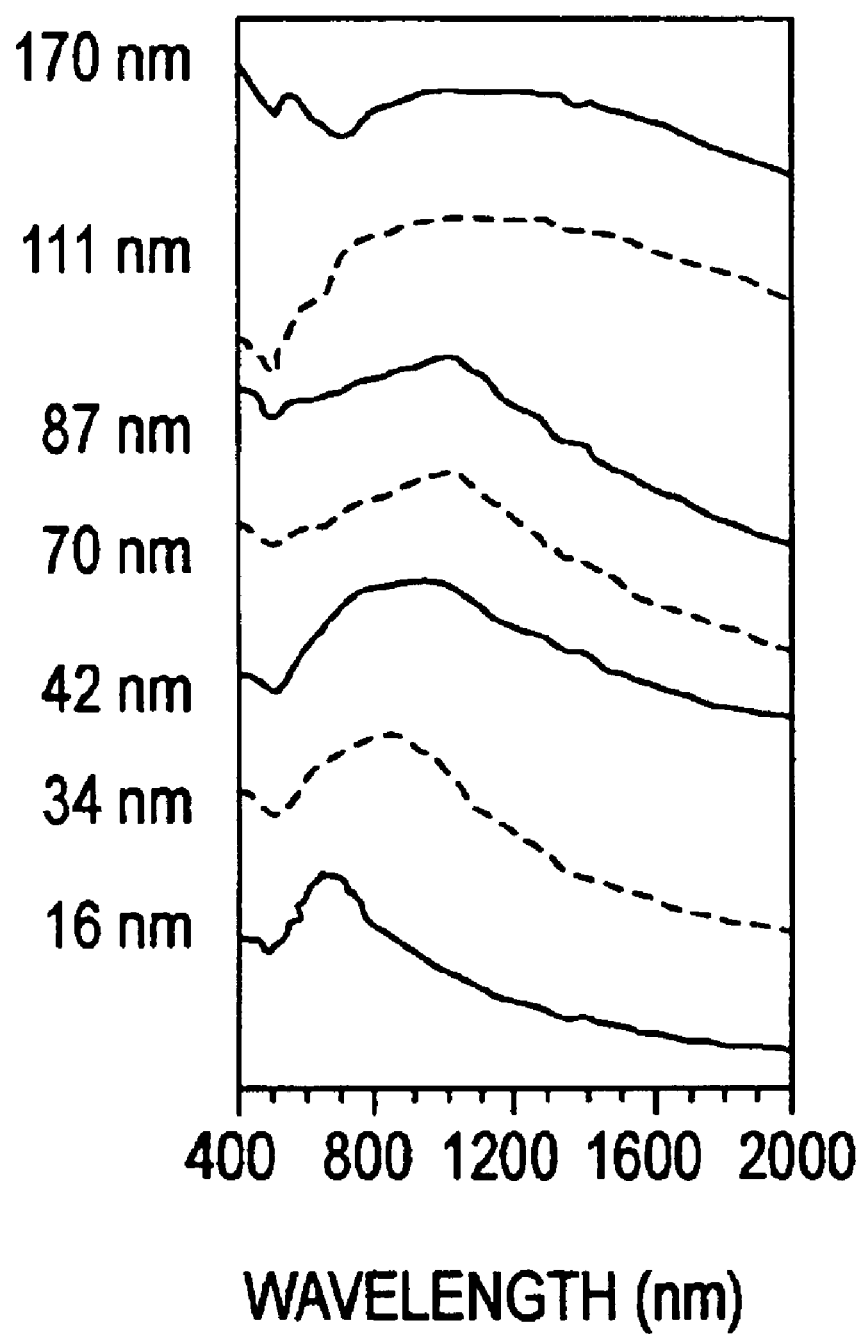
FIG. 2 includes extinction spectra of large gold nanoparticle planar arrays on smooth quartz substrates for nanoparticle sizes of 16, 34, 42, 70, 87, 111, and 170 nm. Substrates were oriented with the arrays facing the light source to minimize interferometric fringe effects. Inflections in the spectra at 630 and 1400 nm are artifacts from instrumentation. Spectral intensities have been modulated for clarity in presentation with minimal effect on the extinction maxima.

Considered here are the SERS properties of highly ordered, close-packed arrays of large (16–170 nm) gold nanoparticles. The SERS activities from these substrates are tunable as a function of both periodic nanostructure and incident wavelength, with empirical signal enhancement factors (G) ranging from $10^4$ to over $10^7$. The gold nanoparticles in the mid-nanometer size regime (e.g. 15–200 nm) are capable of self-organizing into planar close-packed arrays when treated with resorcinarene tetrathiol 2 as described above. The nanostructured films vary in their optical reflectivities and absorptivities, changing in hue from blue to a faint grey. Extinction spectra reveal size-dependent shifts in dipolar plasmon resonance by hundreds of nanometers from the visible to the near infrared (NIR) region (see FIG. 2). The dramatic changes in extinction as a function of periodicity suggest that the arrays are comparable to metallic thin films whose plane surface plasmons have been localized by periodic gratings, and whose optical properties also vary as a function of periodic structure and incident wavelength.

The SERS properties of the large gold nanoparticle arrays were evaluated by comparing relative changes in the Raman signal intensities of adsorbed tetrathiol resorcinarene 2. Spectra were obtained from three instruments with different configurations and excitation wavelengths ($\lambda_{ex}$) but approximately equal solid angles of collection as defined by their effective numerical apertures (N.A.): a dispersive spectrometer operating at 647.1 nm, a home-built Raman imaging microscope operating at 785 nm (A. D. Gift et al., Raman Spectra, 30, 757–765 1999), and an FT spectrometer operating at 1064 nm (see FIGS. 3A, 3B). Empirical signal enhancement factors (G) were determined using peak integration ratios of the surface-enhanced Raman vibration of tetrathiol resorcinarene 1 at 813 cm$^{-1}$ to the corresponding unenhanced signal from noncrystalline films of defined thickness, with values ranging from $10^4$ to over $10^7$ (see FIGS. 3C, 3D). It must be noted that the measurements are macroscopic with respect to the periodicity of the arrays and do not necessarily correlate with localized signal enhancements, which may be several orders of magnitude greater than the spatially averaged factors (see below). However, the G values reported here are practical for defining minimum signal enhancements and can be used to evaluate periodic trends.

Overall, unit particle size and excitation wavelength are found to be strongly correlated with the SERS activity of the arrays (see FIG. 3C). The extinction maxima of the arrays with the highest SERS activities do not correlate strongly with $\lambda_{ex}$, which suggests significant contributions by other means. These include scattering efficiency, which is known to increase with particle diameter to the fourth power in isolated metal particles, and signal amplification by plasmon modes resonant at the Stokes-shifted Raman wavelength $\lambda_{sr}$ which can differ from $\lambda_{ex}$ by as much as 100 nm for the vibrational band of interest.

Interestingly, the empirical enhancement factors demonstrate a strong dependency on the solid angle of collection. Micro-Raman spectra obtained at 785 nm, excitation using objective lenses with N.A.s of 0.25, 0.40, and 0.75 yielded G values that varied by nearly an order of magnitude (see FIG. 3D). The effective Raman scattering cross section ($\beta$) of unenhanced samples did not change with aperture by more than a factor of 50%, confirming the surface-enhanced nature of the phenomenon. Values for $\beta$ are often dependent on the angle of observation and also the angle of incidence, which have a strong influence on the electric field intensity at metal surfaces. Raman scattering studies of adsorbates on smooth and electrochemically silver surfaces have demonstrated marked changes in signal intensities as a function of observation angle, with a maximum between 55° and 60° relative to the surface normal. In comparison, the maximum half-angles from the objective lenses above are 15°, 24°, and 49° respectively, which correlate well with the considerable increases in G.

Figure 7:
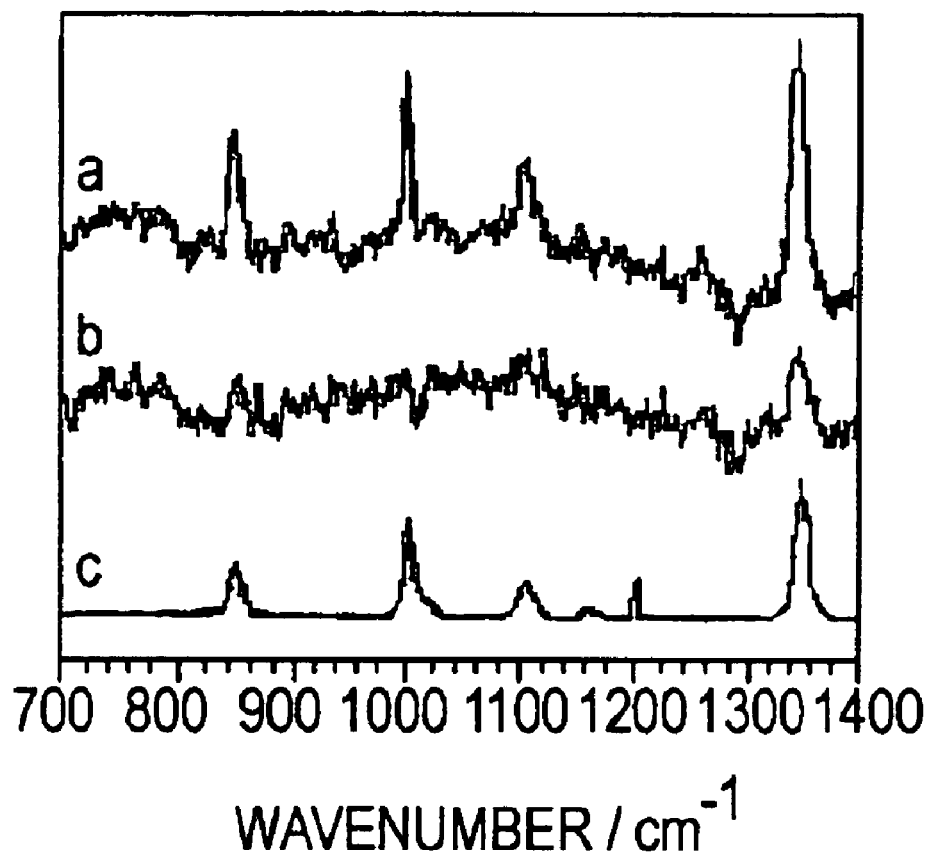
FIG. 7 shows SERS difference spectra of nitrobenzene adsorbed to resorcinarene-encapsulated 170 nm particle array. Spectra were obtained using a dispersive Raman microscope with a 20× objective lens at an excitation wavelength and irradiation time of 30 seconds. Spectra a and b have been shifted and magnified for clarity of presentation. Difference spectra a is after 5 minute exposure to nitrobenzene vapor. Difference spectra b is after exposure to 30 mL of nitrobenzene-saturated air. Spectra c is Raman spectra of neat nitrobenzene. Peak assignments ($cm^{-1}$) are as follows: 854, $\beta$ ($NO_2$); 1005 $v_{12}$ (arom); 1110 $v_{13}$ (arom); 1345 $v_s$ ($NO_2$).

The resorcinarene-coated nanoparticle arrays are able to detect volatile organic compounds with spectroscopic precision and thus have promise as chemical sensors. Passage of approximately 30 mL of nitrobenzene-saturated air through a flow cell containing the 170-nm particle arrays resulted in the appearance of new peaks by SERS (see FIG. 7). Signal intensities in the Raman difference spectra increased with further vapor exposure and are clearly associated with the vibrational modes of nitrobenzene (see FIG. 7). The analyte presumably adsorbs to the resorcinarene surfactant layer in a nonspecific manner, so that its signal is enhanced solely by the electromagnetic field of the underlying nanostructured substrate. Other surfactant-coated SERS substrates have also demonstrated detection of organic analytes in gaseous and aqueous environments, with heightened sensitivity and/or selectivity in some cases.

Theoretical studies on aggregate structures suggest that the electromagnetic field effects responsible for SERS are localized in the interstitial regions of the arrays, accompanied by field depletion outside of these areas. Recent SERS analyses of 50–60 nm metal colloid aggregates allege that NIR excitation produces giant local field effects corresponding to Raman enhancement factors on the order of $10^{11}$ or more. This implies that the great majority of the SERS signal from the arrays is due to the excitation of a very small percentage of adsorbate at these interstitial sites, and that their true enhancements are greater than the surface-averaged G values by several orders of magnitude. Theoretical models of electromagnetic field intensities in periodic metal gratings offer additional insights: the field enhancements within the channels are predicted to increase commensurately with aspect ratio, and to resonate at wavelengths determined by the grating amplitude. Such models are congruent with the size-dependent SERS activities of the nanoparticle arrays: the interparticle spacings resemble grating channels with amplitudes and aspect ratios that vary as a function of periodic structure.

Some practical aspects of the large gold nanoparticle arrays pursuant to the invention follow. The nanostructured films of the invention are stable in air and water at ambient temperatures and show no appreciable loss in SERS activity over a period of several months. The adsorption of volatile analytes is reversible, such that the substrates can be used multiple times. In addition, the SERS enhancements are reproducible for different sites on a given substrate as well as between replicate samples, with relative standard deviations of 14 to 35% (see FIG. 3D).

As described above, an embodiment of the invention enables large (15–200 nm) gold particles to self-organize at the air-water interface into monoparticulate films that can subsequently be transferred onto hydrophilic substrates as 2D hexagonal close-packed (hcp) arrays. The calixarene surfactant effects stabilization of these nanoparticle ensembles; i.e. the calixarene surfactant layer is required to be highly repulsive at close range but thin enough to maintain minimal interparticle separations, a critical parameter in the electromagnetic properties of metal nanoparticle assemblies. Short-range repulsion can be enhanced by creating a surfactant layer with (i) hydrophobic chains of uniform length at intermediate packing densities, such that their relatively high conformational entropies increase the barrier against steric compression, and (ii) an appreciable surface charge density for generating repulsive electrostatic double-layer forces. These features also render the encapsulated nanoparticles amphiphilic and promote self-organization at the air-water interface. Calix resorcinarenes are excellent surfactants for steric stabilization.

The large gold nanoparticle arrays have several other important qualities that complement their size-tunable optical properties. The arrays are stable in air at ambient temperatures and generate reproducible Raman signal intensities over a period of several months. The fabrication and transfer methods are straightforward and applicable to a variety of surfaces for a diverse range of optical functions. The arrays are nanoporous by nature and may be used to isolate and study individual proteins and other macromolecules. Such practical features enhance the value of the nanoparticle arrays as substrates for applications involving SERS and other surface-enhanced optical phenomena.

Figure 8:
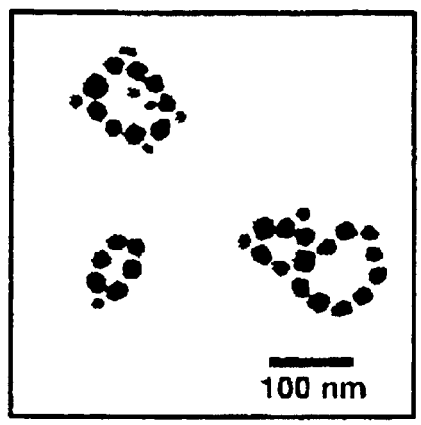
FIG. 8 is a representation of a transmission electron micrograph (TEM) of a self-assembled 2D nanoparticle array of encapsulated cobalt (Co) particles pursuant to the invention where ring-like bracelets are self-assembled.

The invention is not limited to making highly ordered monoparticulate planar arrays of gold particles and can be practiced using other metal nanoparticles. For purposes of further illustration and not limitation, self-assembled rings of weakly ferromagnetic Co nanoparticles (27 nm diameter) were treated with tetrathiol resorcinarene 4 and dispersed in toulene. The resorcinarene encapsulated nanoparticles self-assembled into 2D ring-like bracelets, and could be deposited onto carbon-coated TEM grids (see FIG. 8). The Co nanoparticle rings may exhibit useful magnetic properties (e.g. stable chiral magnetic domains) as a result of the collective behavior of magnetic dipoles in cyclic configurations.

Figure 9:
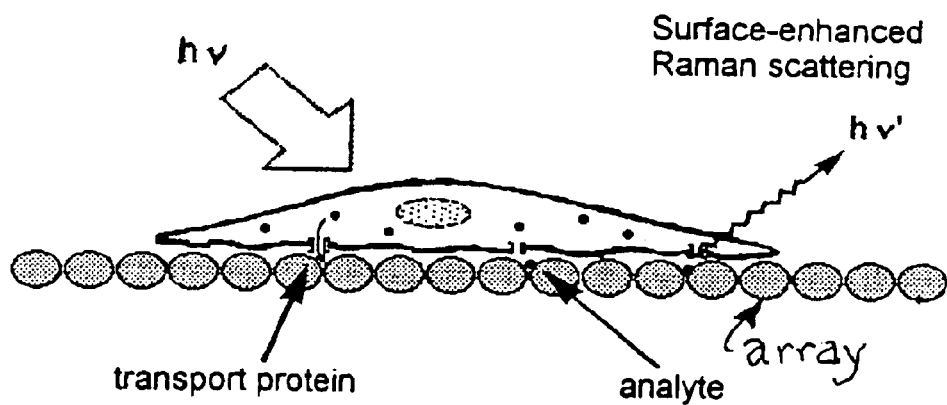
FIG. 9 is a schematic view of a nanoparticle array as SERS-based sensor of cell afflux activity.

Another embodiment of the invention envisions using the resorcinarene-encapsulated planar arrays described above as substrates for cell adhesion. It has been determined that several cell lines (BEK 293, HeLa, and pancreatic $\beta$-cells) adhere strongly and remain viable on the order of days on the gold nanoparticle arrays described above. The nanoparticle arrays can be used to detect exogenous analytes as illustrated in FIG. 9, albeit at relatively high concentrations. The methods described above can be used to fabricate gold nanoparticle arrays with greater interparticle spacings, which should delocalize field effects and produce larger sampling volumes for lower detection limits.

Figure 10:
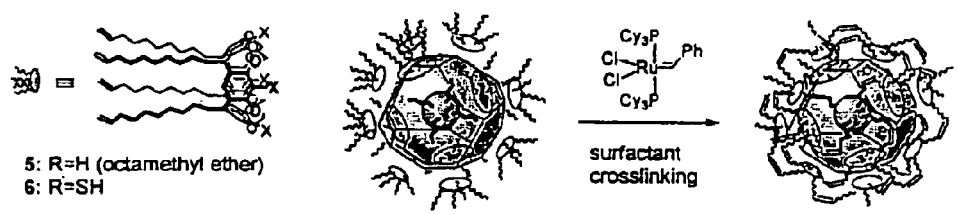
FIG. 10 is a diagram of a gold nanoparticle being treated with resorcinarene 5 or 6 which is then cross-linked.

Still another embodiment of the invention envisions cross-linking the resorcinarene surfactant layer on the encapsulated nanoparticles. As illustrated in FIG. 10, tetraalkene resorcinarene 5, whose tails can be cross-linked by olefin metathesis, can be used as the encapsulating layer on the nanoparticles. Gold nanoparticles encaged in cross-linked shells were found to be resistant to precipitation-induced fusion, and could even survive passage through a polystyrene size exclusion column. In lieu of tetraalkene resorcinarene 5, tetrathiol resorcinarene 6 of FIG. 10 can be used in which cross-linking and polyvalent chemisorption operate synergistically to provide a robust, nondesorptive surfactant shell. Gold nanoparticles (20 nm) encapsulated by resorcinarene 6 were found to be highly resistant to surface desorption when treated with olefin metathesis catalyst at low concentrations, while retaining excellent dispersibility in organic solvents. These can be precipitated and redispersed repeatedly in nonpolar solvents such as toulene and chloroform, and can be functionalized with organic or biologically active ligands for site-directed nanoparticle delivery.

Synthesis Procedures

Synthesis of Tetrabenzylthiol Resorcinarene 1

Tetra-2,2',2",2'"-methylresorcinarene. 2-methylresorcinol (0.687 g, 5.53 mmol) and dodecanal (1.2 mL, 5.44 mmol) were dissolved in EtOH (4 mL) and cooled to 0° C. in an ice water bath. HCl (4 N, 4.7 mL) was added dropwise and the reaction mixture was stirred for 10 minutes, then heated to 80° C. Within 10 min a yellow precipitate was observed. The reaction mixture was stirred for 4 days, then cooled to room temperature and poured into 40 mL of $H_2O$. The resulting precipitate was filtered, washed with water, then partially dispersed in MeOH and precipitated to yield tetramethylresorcinarene as a yellow solid (0.863 g, 55% yield). IR (neat, cm$^{-1}$): 3362 (br), 2916, 2849, 1474, 1458, 1335, 1095. $^1$H-NMR (DMSO-d$_6$, 300 MHz): δ 8.65 (s, 8 H), 7.18 (s, 4 H), 4.20 (t, J=7.2 Hz, 4 H), 2.16 (m, 8 H), 1.94 (s, 12 H), 1.24 (m), 0.86 (t, J=6.9 Hz, 12 H).

Tetramethylcavitand resorcinarene. Tetramethylresorcinarene (0.482 g, 0.415 mmol) was dissolved in anhydrous DMF (21 mL) in a heavy-walled pressure reaction vessel. Bromochloromethane (1.1 mL, 16.9 mmol) and $Cs_2CO_3$ (3.116 g, 9.56 mmol) were added and the reaction mixture was heated at 90° C. for 7.5 h. The reaction mixture was cooled to room temperature and poured into HCl (100 mL, 2 N) and extracted with dichloromethane (3×70 mL). The organic layer was washed with HCl (2 N, 2×75 mL), water (100 mL), then dried over magnesium sulfate and concentrated to dryness. Silica gel chromatography (hexanes/dichloromethane) yielded the desired cavitand resorcinarene as a white solid (0.352 g, 70% yield). IR (neat, cm$^{-1}$): 2926, 2853, 1468, 1430, 1398, 1304, 1234, 1151, 1091, 1022, 980, 760. $^1$H-NMR (CDCl$_3$, 300 MHz): δ 7.00 (s, 4 H), 5.93 (d, J=6.9 Hz, 4 H), 4.77 (t, J=7.8 Hz, 4 H), 4.27 (d, J=6.9 Hz, 4 H), 2.22 (m, 8 H), 1.99 (s, 9 H), 1.28 (m), 0.90 (t, J=6.3 Hz, 12 H). $^{13}$C-NMR (CDCl$_3$, 75 MHz): δ 153.47, 138.17, 123.80, 117.82, 98.72, 37.20, 32.18, 30.36, 30.10, 29.95, 29.63, 28.21, 22.93, 14.33, 10.54.

Tetra-2,2', 2",2'"-(bromomethyl)cavitand resorcinarene. Tetramethylcavitand (0.094 g, 0.101 mmol) was dissolved in CCl$_4$ (3 mL) and treated with N-bromosuccinimide (0.101 g, 0.5674 mmol) and azo-bisisobutyronitrile (0.014 g, 0.085 mmol). The reaction mixture was heated to reflux at 85° C. for 5.5 h under an argon atmosphere. The reaction mixture was then cooled to room temperature, diluted with dichloromethane (40 mL), washed with water (2×40 mL), dried over magnesium sulfate and concentrated to dryness. Silica gel chromatography (EtOAc/hexanes) yielded the desired tetra(bromomethyl) resorcinarene as a white solid (0.088 g, 74% yield). IR (neat, cm$^{-1}$): 2925, 2853, 1471, 1454, 1242, 1148, 1014, 974, 941, 668. $^1$H-NMR (CDCl$_3$, 300 MHz): δ 7.14 (s, 4 H), 6.03 (d, J=6.3 Hz, 4 H), 4.79 (t, J=7.8 Hz, 4 H), 4.57 (d, J=6.9 Hz, 4 H), 4.43 (s, 8 H), 2.21 (m, 8 H), 1.28 (m), 0.89 (t, J=6 Hz, 12 H). $^{13}$C-NMR (CDCl$_3$, 75 MHz): δ 153.78, 138.28, 124.81, 121.27, 99.37, 37.02, 32.14, 29.91, 29.60, 28.07, 22.90, 14.32. PDMS: expected for $C_{80}H_{116}O_8Br_4$=1525.4, observed=1525.7.

Tetrabenzylthiol resorcinarene 1. Tetra(bromomethyl) resorcinarene (0.258 g, 0.169 mmol) was dissolved in degassed DMF (11 mL) and treated with thiourea (0.082 g, 1.08 mmol). The reaction mixture was heated to 80° C. under Ar atmosphere and stirred for 12 hours. The reaction mixture was cooled to room temperature and poured into degassed NaOH solution (1 M, 40 mL), resulting in a white precipitate. The reaction mixture was stirred for 1 hour, then cooled to 0° C. and acidified to pH 2 and extracted with EtOAc (3×50 mL). The organic layer was washed with $H_2O$ (2×75 mL), dried over magnesium sulfate and concentrated to dryness. Silica gel chromatography (EtOAc/hexanes) yielded the desired tetrabenzylthiol resorcinarene 1 as a white solid (0.152 g, 67% yield). IR (neat, cm$^{-1}$): 2924, 2852, 1469, 1016, 982. $^1$H-NMR (CDCl$_3$, 300 MHz): δ 7.07 (s, 4 H), 5.97 (d, J=6.9 Hz, 4 H), 4.76 (t, J=7.8 Hz, 4 H), 4.48 (d, J=7.2 Hz, 4 H), 3.59 (d, J=7.5 Hz, 8 H), 2.2 (m, 8 H), 1.90 (t, J=7.5 Hz, 4 H), 1.28 (m), 0.90 (t, J=6 Hz, 12 H). $^{13}$C-NMR (CDCl$_3$, 125 MHz): δ 153.12, 138.36, 127.40, 119.54, 100.13, 37.22, 32.16, 30.45, 30.05, 29.92, 29.60, 28.14, 22.90, 18.32, 14.29. PDMS: expected for $C_{80}H_{120}O_8S_4$=1338.1, observed=1338.7.

Synthesis of Tetraarylthiol Resorcinarene 2

Tetraarylthiol resorcinarene 2. Tetrabromocavitand resorcinarene was prepared by a modification of literature procedures.[1] Tetrabromocavitand resorcinarene (0.576 g, 0.394 mmol) was azeotroped several times with toluene in a 2-neck round-bottomed flask. The reaction flask was connected with a sidearm containing freshly sublimed sulfur (0.202 g, 6.304 mmol), then dried under $P_2O_5$ in vacuo overnight. The reaction flask was released to argon and treated with anhydrous THF (15 mL), then cooled to −78° C. and treated with n-BuLi (1.83 mL, 2.16 M in hexanes). The reaction mixture was stirred for 10 min at −78° C., then treated with dry sulfur and slowly warmed to room temperature over a 6-hour period. The reaction mixture was treated with saturated aqueous $Na_2S_2O_3$ solution (15 mL), then diluted with water (150 mL) and extracted with EtOAc (3×50 mL). The combined organic extracts were dried over magnesium sulfated and concentrated to dryness. Silica gel chromatography (EtOAc/hexane) yielded the desired tetraarylthiol resorcinarene 2 as a white solid (0.432 g, 85% yield). IR (neat, cm$^{-1}$): 2925, 2854, 1466, 1417, 1092. $^1$H NMR (300 MHz, CDCl$_3$): δ 6.86 (s, 4 H), 5.96 (d, 4 H, J=6.9 Hz), 4.7 (t, 4H, J=8.1 Hz), 4.37 (d, 4 H, J=7.2 Hz), 3.78 (s, 4 H), 2.2–2.0 (m, 8 H), 1.5–1.2 (m, 72 H), 0.90 (t, 12 H, J=6.5 Hz). $^{13}$C NMR (CDCl$_3$, 75 MHz): δ 150.40, 138.46, 121.91, 98.53, 37.47, 32.21, 29.97, 29.66, 28.07, 22.96, 14.38. Anal. Calcd for $C_{72}H_{112}S_4$; C, 71.21; H, 8.81; S, 10.00. Found C, 71.42; H, 8.75; S 10.02.

[1] (a) Moran, J. R.; Karbach, S.; Cram, D. J. *J. Am. Chem. Soc.* 1982, 104, 5826–28.(b) Cram, D. J.; Karbach, S.; Kim, H.-E.; Knobler, C. B.; Maverick, E. F.; Ericson, J. L.; Helgeson, R. C. *J. Am. Chem. Soc.* 1988, 110, 2229–37.

Although the invention has been described with respect to certain embodiments, those skilled in the art will appreciate that changes, modifications can be made thereto without departing from the scope of the invention as set forth in the appended claims.

We claim:

1. A method for dispersing nanoparticles in a liquid medium by treating said nanoparticles with calixarene surfactant comprising calixarene having a headgroup with tetracarbon substituents adsorbed on the nanoparticles.

2. The method of claim 1 wherein said calixarene comprises a resorcinarene having a headgroup with tetracarbon substituents comprising thiol.

3. The method of claim 1 wherein said nanoparticles are encapsulated in a nondesorptive shell comprising a crosslinked calixarene.

4. A method of making a self-assembly of nanoparticles by dispersing said nanoparticles in a liquid medium using the method of claim 1.

5. A method of making a self-assembly of nanoparticles by dispersing said nanoparticles in a liquid medium using the method of claim 1, forming a self-assembly of the treated nanoparticles, and then transferring said self-assembly onto a substrate.

6. A method for making a two-dimensional array of particles on a substrate, comprising treating the particles with a calixarene having a headgroup with tetracarbon substituents adsorbed on the particles, effecting self-assembly of the treated particles, and depositing the treated, self-assembled particles on a substrate as a two dimensional array.

7. The method of claim 6 wherein the particles are treated by reaction with calixarene molecules.

8. The method of claim 6 wherein the calixarene comprises a resorcinarefle having a large, concave headgroup with tetracarbon substituents adsorbed on the particles.

9. The method of claim 8 wherein the resorcinarene comprises tetrathiol resorcinarene having a headgroup with tetracarbon substituents comprising thiol.

10. The method of claim 6 wherein the particles are metallic.

11. The method of claim 6 wherein the particles have a diameter of 15 to 200 nm.

12. A two-dimensional particle assembly on a substrate wherein said assembly comprises calixarene-treated particles wherein the calixarene-treated particles comprise calixarene having a headgroup with tetracarbon substituents adsorbed on the particles.

13. The array of claim 12 wherein the particles comprise resorcinarene-treated particles wherein the resorcinarene-treated particles comprise resorcinarene having a headgroup with tetracarbon substituents adsorbed on the particles.

14. The array of claim 12 wherein the particles are metallic and have a diameter of 15 to 200 nm.

15. A chemical or biomolecular sensor including the assembly of claim 12.

16. The two dimensional particle assembly of claim 12 wherein the tetracarbon substituents comprise thiol.

* * * * *